United States Patent [19]

Kawatsura et al.

[11] Patent Number: 6,072,073

[45] Date of Patent: Jun. 6, 2000

[54] CARBONYL ARYLATIONS AND VINYLATIONS USING TRANSITION METAL CATALYSTS

[75] Inventors: Motoi Kawatsura; John F. Hartwig, both of New Haven, Conn.

[73] Assignee: Yale University, New Haven, Conn.

[21] Appl. No.: 09/376,898

[22] Filed: Aug. 18, 1999

Related U.S. Application Data

[60] Provisional application No. 60/097,472, Aug. 21, 1998.

[51] Int. Cl.[7] ...................... C07C 255/07; C07C 303/16; C07C 45/37
[52] U.S. Cl. .............................. 560/82; 560/12; 568/312; 568/317; 558/371
[58] Field of Search ............................... 558/371; 560/12, 560/82; 568/312, 317

[56] References Cited

PUBLICATIONS

Ozawa, fumuyuki et al., Palladium–Catalyzed Double Carbonylation of Aryl Halides Affording alpha–keto Amides. (1986), 51, pp415–417.

*Primary Examiner*—Joseph McKane
*Assistant Examiner*—Ebenezer Sackey
*Attorney, Agent, or Firm*—Wiggin & Dana

[57] ABSTRACT

The invention is directed to a process for preparing an alpha-arylated or vinylated carbonyl-containing compounds, comprising reacting a compound having a carbonyl group with an arylating or vinylating compound in the presence of a base and a transition metal catalyst. The transition metal catalyst has the formula $X_nM(ER_{1-4})_m$, wherein X is an optional ligand, M is a group 8 transition metal, E is an element bearing a nonbonding electron pair when E is not bonded to the metal, and R is a substituent bonded to E through a carbon, nitrogen, oxygen, or sulfur atom, with the proviso that $R_3$ cannot contain 3 aryl groups, n is an integer from 0 to 4, and m is an integer from 1–4. The process of the invention is useful for preparation of alpha-arylated or vinylated carbonyl-containing compounds which are significant in the development of pharmacologically active compounds and polymers and oligomers.

21 Claims, No Drawings

CARBONYL ARYLATIONS AND VINYLATIONS USING TRANSITION METAL CATALYSTS

CROSS-REFERENCE TO RELATED APPLICATIONS

This application claims the benefit of U.S. Provisional Application No. 60/097,472 filed Aug. 21, 1998.

FIELD OF THE INVENTION

This invention relates to a general process for alpha-arylation or vinylation of carbonyl-containing compounds, and more particularly to a general process for synthesizing alpha-arylated or -vinylated carbonyl-containing compounds from arylating or vinylating compounds and carbonyl containing compounds using a transition metal catalyst.

DESCRIPTION OF THE RELATED ART

The palladium-catalyzed coupling to form C—C bonds between aryl and vinyl halides or triflates and a carbon nucleophile is one of the most widely used transition metal-catalyzed reactions. (Stille, J. K. *Angew. Chem., Int. Ed. Engl.*, 25:508–524 (1986); Miyaura, N. et al., *Chem. Rev.*, 95:2457–2483 (1995); Negishi, E. *Acc. Chem. Res.*, 15:340–348 (1982)). The related cross-coupling reactions involving ketone enolates as the nucleophile are also very important commercially. However, this class of cross-coupling reaction has been limited to tin enolates, silyl-enol ethers in combination with tin fluoride, intramolecular examples, or examples with acid ketones and metal ion catalysts in low yields (Kosugi, M. et al., *Bull. Chem. Soc. Jpn.*, 57:242–246 (1984)).

Many transition metal-catalyzed approaches to ketone arylation using pre-formed main group enol ethers (Carfagna, C. et al., *J. Org. Chem.*, 56:261–263 (1991); Durandetti, M. et al., *J. Org. Chem.* 61:1748–1755 (1996); Fauvargue, J. F. et al., *J. Organomet. Chem.*, 177:273–281 (1979)) or bismuth or lead reagents (Barton, D. H. R. et al., *Tet. Letters,* 27:3619–3522 (1986); Barton, D. H. R. et al.,*J. Chem. Soc., Perkin Trans.* 1:1365–1375 (1992)) have been investigated. However, use of toxic main-group reagents, low product yields, and multi-step preparation of compounds make these procedures particularly difficult to exploit commercially. In addition, arylation using a metal halide in the absence of a chelating ligand has been shown (Satoh et al., *Angew. Chem. Int. Ed. Engl.* 36:1740–1741 (1997)); however, the yield of product is unacceptably low for commercial purposes.

It would be advantageous to prepare alpha-aryl carbonyl-containing compounds from arylating compounds such as aryl halides and/or aryl sulfonates because aryl halides are generally inexpensive and readily available, while aryl sulfonates are easily prepared from phenols.

U.S. patent application Ser. No. 09/173,527 discloses a transition metal catalyzed process for preparing arylated carbonyl-containing compounds. However, this process uses chelating ligands as part of the catalyst, and such chelating ligand catalysts may not be useful in many synthetic preparations.

In view of the above, a need exists for a general and efficient process of synthesizing alpha-aryl carbonyl-containing compounds. The discovery and implementation of such a process would simplify the preparation of commercially significant organic alpha-aryl carbonyl-containing compounds and would enhance the development of novel pharmacologically active compounds. The present invention is believed to be an answer to that need.

SUMMARY OF THE INVENTION

In one aspect, the present invention is directed to a process for preparing alpha-arylated or -vinylated carbonyl-containing compounds, comprising the step of reacting a compound having at least one carbonyl group with an arylating or vinylating compound in the presence of a base and a transition metal catalyst under reaction conditions effective to form the alpha-arylated or -vinylated carbonyl-containing compound, the transition metal catalyst having the formula $X_nM(ER_{1-4})_m$, wherein X is an optional ligand, M is a group 8 transition metal, E is an element bearing a nonbonding electron pair when E is not bonded to the metal, and R is a substituent bonded to E through a carbon, nitrogen, oxygen, or sulfur atom, with the proviso that $R_3$ cannot contain 3 aryl groups, n is an integer from 0 to 4, and m is an integer from 1–4.

These and other aspects will become apparent upon reading the following detailed description of the invention.

DETAILED DESCRIPTION OF THE INVENTION

It now has been surprisingly found, in accordance with the present invention, that a solution is provided to the problem of providing a general and efficient process of synthesizing alpha-arylated or -vinylated carbonyl-containing compounds from a starting material having at least one carbonyl group, and an arylating or vinylating compound. The present inventors have solved this problem by utilizing reaction conditions that include a base and a transition metal catalyst having the formula $$X_nM(ER_{1-4})_m$$

wherein X is an optional ligand, M is a group 8 transition metal, E is an element bearing a nonbonding electron pair when E is not bonded to the metal, and R is a substituent bonded to E through a carbon, nitrogen, oxygen, or sulfur atom, with the proviso that $R_3$ cannot contain 3 aryl groups, n is an integer from 0 to 4, and m is an integer from 1–4. The process of the present invention provides a general process for production of alpha-arylated carbonyl-containing compounds, a class of compound which is particularly significant in the development of pharmacologically active compounds and production of polymers and oligomers.

As defined herein, "alpha-carbon" refers to the carbon atom directly adjacent to a carbonyl (C=O) group in an organic molecule. The phrases "alpha arylation", "alpha arylating", and "alpha arylated" refer to attachment of an aryl group onto the alpha carbon of an organic compound. Similarly, the phrases "alpha vinylation", "alpha vinylating", and "alpha vinylated" refer to attachment of a vinyl group onto the alpha carbon of an organic compound. The terms "aryl" and "aryl group" are defined as a compound or compounds whose molecules have the ring structure characteristic of benzene, naphthalene, phenanthroline, anthracene, pyridine, furan, indole, and the like. The term "vinyl" and "vinyl group" are defined herein as a group containing a C—C double bond, that includes the carbon attached to an alpha carbon. The phrase "nonbonding electron pair" refers to a pair of electrons on an atom that do not participate in covalent bond formation.

The process of the present invention is directed to the synthesis of alpha-arylated and -vinylated carbonyl-containing compounds, particularly alpha-arylated ketones and malonates. The process of the invention comprises reacting a compound having at least one carbonyl (C=O) group with an arylating or vinylating compound in the presence of a base and a transition metal catalyst under reaction conditions effective to form an alpha-arylated or -vinylated carbonyl-containing compound. The transition metal catalyst has the formula

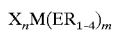

wherein X is an optional ligand, M is a group 8 transition metal, E is an element bearing a nonbonding electron pair when E is not bonded to the metal, and R is a substituent bonded to E through a carbon, nitrogen, oxygen, or sulfur atom, with the proviso that $R_3$ cannot contain 3 aryl groups, n is an integer from 0 to 4, and m is an integer from 1–4.

More specifically, the process of this invention can be represented by Scheme I:

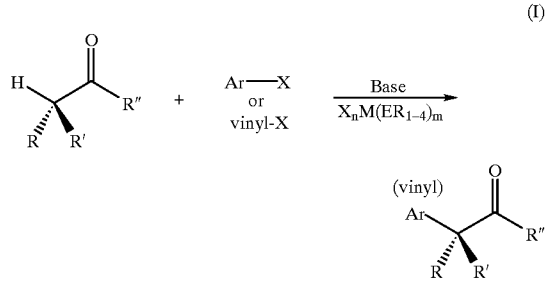

Briefly, in Scheme I, an arylating (Ar-X) or vinylating (vinyl-X) compound is reacted with a carbonyl-containing compound in the presence of a base, a chelating ligand ($ER_{1-4}$), and a Group 8 metal (M) to form an alpha-arylated carbonyl-containing compound. This reaction and each of the components are described in more detail below.

The arylating compound used in the process of the present invention may be any 5, 6, or 7-membered aryl ring structure, including heterocyclic ring structures, that include an activated group, such as a leaving group. In one embodiment, the arylating compound has the structure of formula (II):

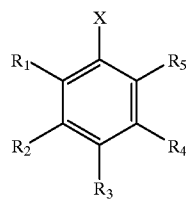

In formula (II), X may be any halide atom (F, Cl, Br, I), or any sulfur-containing leaving group (e.g., triflate, sulfonate, tosylate, oxygen, and the like) known in the art. Bromides and chlorides are especially preferred in the process of the present invention. $R_1$, $R_2$, $R_3$, $R_4$, and $R_5$ are independently selected from H; CN; alkyl, such as methyl, ethyl, propyl, n-butyl, t-butyl, and the like; formyl; $CF_3$; $CCl_3$; $C_6H_5$; amide such as $C(O)N(CH_3)_2$, $C(O)N(CH_2CH_3)_2$, $C(O)N(CH_2CH_2CH_3)_2$, and the like; acyl, such as $C(O)$—$C_6H_5$, and the like; ester, aryl, alkoxy, amino, thioalkoxy, phosphino, vinyl, halide, and the like. In an alternative embodiment, one or more of $R_1$, $R_2$, $R_3$, $R_4$, and $R_5$ may be joined to form a heterocyclic structure.

Arylating and vinylating compounds that are also useful in the method of the invention include any molecule such as that shown in formulaa (II) that contains an activated aryl or vinyl group. As used herein, the term "activated" refers to conventional leaving groups at position X such as halide atoms (F, Cl, Br, I), any oxygen-containing leaving group such as a sulfonate (triflate, tosylate, and the like), phosphate or phosphate esters, actates, any other leaving group X whose conjugate acid HX has a $pK_a$ less than 16, or other leaving groups known in the art.

Exemplary activated aryl and vinyl groups useful in the present invention include substituted or unsubstituted aryl halides (e.g., bromobenzene or chlorobenzene), vinyl halides, substituted or unsubstituted aryl sulfonates, vinyl sulfonates, vinyl tosylates, vinyl phosphates, and the like.

Preferred arylating compounds used in the process of the invention include aryl halides such as bromobenzene, 4-bromo-benzonitrile, 4-bromo-t-butyl benzene, 3-bromo-methoxy benzene, 2-bromo toluene, para-formyl phenyl bromide, p-$CF_3$ phenyl bromide, p-phenyl phenyl bromide, p-$C(O)N(CH_2CH_3)_2$ phenyl bromide, and p-$C(O)$-$C_6H_5$ phenyl bromide.

According to the process of the invention, compounds containing at least one carbonyl group include any carbonyl-containing compound that possesses an alpha-carbon. The structure of a preferred set of carbonyl-containing compounds is

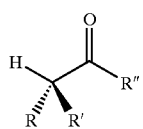

where R and R' are independently selected from hydrogen, alkyl, aryl or heteroaryl, alkoxo, vinyl, alkyl, or amido; and R" is hydrogen, aryl or heteroaryl, alkoxo, vinyl, alkyl, or amido. Preferred aryl and heteroaryl groups for R" include phenyl, pyrrole, N-substituted pyrrole, furan, thiophene, and the like.

Exemplary carbonyl-containing groups include ketones, amides, esters, carboxylic acids, thioesters, amidines, anhydrides; β-dicarbonyl compounds such as malonates, acetoacetates, β-diketones, and the like; and α-dicarbonyl compounds, such as α-diketones, α-ketoesters, α-ketamides, and the like. Additional useful compounds include malononitriles, compounds with carbonyl groups β-to sulfoxides, sulfones, phosphates, phosphate esters, and nitrites. Particularly useful carbonyl-containing compounds include alkyl aryl ketones, such as acetophenone, propiophenone, isobutyrophenone, and dialkyl ketones, such as acetone and diethyl ketone.

The base shown in Scheme I is required for the process of the present invention. Any base may be used so long as the process of the invention proceeds to the alpha-aryl product. It may be important in this regard that the base does not displace all of the chelating ligands on the catalyst. Nuclear magnetic resonance, infrared, and Raman spectroscopies, for example, are useful in determining whether the ligands remain bonded to the Group 8 metal or whether the ligands have been displaced by the base.

Non-limiting examples of suitable bases include alkali metal hydroxides, such as sodium and potassium hydroxides; alkali metal alkoxides, such as sodium t-butoxide; metal carbonates, such as potassium carbonate, cesium carbonate, and magnesium carbonate; alkali metal aryl oxides, such as potassium phenoxide; alkali metal amides, such as lithium amide or lithium diisopropylamide; tertiary amines, such as triethylamine and tributylamine; (hydrocarbyl)ammonium hydroxides, such as benzyltrimethyl-ammonium hydroxide and tetraethylammonium hydroxide; diaza organic bases, such as 1,8-diazabicyclo[5.4.0]-undec-7-ene and 1,8-diazabicyclo-[2.2.2.]-octane, and silyl compounds such as potassium hexamethyldisilazide ($KN(Si(CH_3)_3)_2$). Preferably, the base is an alkali alkoxide or a silyl-containing compound.

The quantity of base which is used can be any quantity which allows for the formation of the alpha-aryl product. Preferably, the molar ratio of base to arylating compound ranges from about 1:1 to about 3:1, and more preferably between about 1:1 and 2:1.

The catalyst, designated $X_nM(ER_{1-4})_m$ in Scheme I, is characterized as comprising a Group 8 transition metal atom or ion (M), a ligand containing an element bearing a nonbinding electron pair (E) when E is not bonded to the metal, and one to four substituents R that are bonded to E through a carbon, nitrogen, oxygen, or sulfur atom. In the catalyst, three aryl groups cannot be used for R, n is an integer from 0 to 4, and m is an integer from 1–4. The catalyst also contains a chiral center and results in a non-racemic chiral catalyst that is capable of generating non-racemic products as shown in more detail in Examples 32–34.

The Group 8 transition metal atom or ion is preferably selected from iron, cobalt, nickel, ruthenium, rhodium, palladium, osmium, iridium, and platinum. More preferably, the Group 8 metal is palladium, platinum, or nickel, and most preferably, palladium. The Group 8 metal may exist in any oxidation state ranging from the zero-valent state to any higher variance available to the metal.

As indicated above, E is an element that contains a nonbinding electron pair when E is not bonded to the metal. Preferred elements for E in the transition metal catalyst include elements from Group 14, Group 15, and Group 16 of the Periodic Table (formerly known as Group IVB, Group VB, and Group VIB, respectively). Preferred elements for E include phosphorus, nitrogen, arsenic, and carbon in the form of a carbene. A particularly preferred element for E is phosphorous.

As indicated above, the R substituents in the catalyst may be any substituent that is bonded to E through a carbon, nitrogen, oxygen or sulfur atom. However, the catalyst of the invention may not have 3 aryl groups. Exemplary groups include t-butyl, cyclohexyl, dialkylamino, o-tolyl, o-anisyl, phenyl, 2-biphenylyl, ferrocenyl and substituted ferrocenyl groups.

Particular catalysts useful in the method of the invention include a combination of bis-(dibenzylideneacetone) palladium, palladium acetate, or palladium dihalides and the ligand $ER_{1-4}$.

Methods for preparing the aforementioned catalysts are known to those skilled in the art. For a description of general synthetic techniques, see *Inorganic Synthesis: Reagents for Transition Metal Complex and Organometallic Systems;* R. J. Angelici, Ed., Wiley-Interscience: New York, 1990, Vol. 28, pp. 77–135 (Chapter 2), incorporated herein by reference, wherein representative preparations of Group 8 complexes containing amine, phosphine, and arsine ligands are taught.

As an alternative embodiment of this invention, the catalyst may be anchored or supported on a support. Useful supports include refractory oxide, such as silica, alumina, titania, or magnesia; charcoal; or an aluminosilicate clay, or molecular sieve or zeolite; or an organic polymeric resin.

The transition metal catalyst may be synthesized first and thereafter employed in the arylation process. Alternatively, the catalyst can be prepared in situ in the arylation reaction mixture. If the latter mixture is employed, then a Group 8 catalyst precursor compound and the desired chelating ligand are independently added to the reaction mixture wherein formation of the transition metal catalyst occurs in situ. Suitable precursor compounds include alkene and diene complexes of the Group 8 metals, preferably, (dibenzylidene)acetone (dba) complexes of the Group 8 metals, as well as, monodentate phosphine complexes of the Group 8 metals, and Group 8 carboxylates. In the presence of the ligand complex, in situ formation of the transition metal catalyst occurs. Non-limiting examples of suitable precursor compounds include [bis-(dibenzylidene)acetone] palladium (0), tetrakis-(triphenylphosphine)-palladium (0), tris-[(dibenzylidene)acetone]palladium (0), tris-[(dibenzylidene) acetone]-dipalladium (0), palladium acetate, and the analogous complexes of iron, cobalt, nickel, ruthenium, rhodium, osmium, iridium, and platinum. Any of the aforementioned catalyst precursors may include a solvent of crystallization. Group 8 metals supported on carbon, preferably, palladium or nickel on carbon, can also be suitably employed as a precursor compound. Preferably, the catalyst precursor compound is bis-[(dibenzylidene) acetone]palladium(0).

The quantity of transition metal catalyst which is employed in the process of this invention is any quantity which promotes the formation of the alpha-aryl product. Generally, the quantity is a catalytic amount, which means that the catalyst is used in an amount which is less than stoichiometric relative to the unsaturated organic sulfonate. Typically, the transition metal catalyst ranges from about 0.01 to about 20 mole percent, based on the number of moles of the carbonyl-containing compound used in the reaction. Preferably, the quantity of transition metal catalyst ranges from about 1 to about 10 mole percent, and more preferably from about 3 to about 8 mole percent, based on the moles of the carbonyl-containing compound.

The process described herein may be conducted in any conventional reactor designed for catalytic processes.

Continuous, semi-continuous, and batch reactors can be employed. If the catalyst is substantially dissolved in the reaction mixture as in homogeneous processes, then batch reactors, including stirred tank and pressurized autoclaves, can be employed. If the catalyst is anchored to a support and is substantially in a heterogeneous phase, then fixed-bed and fluidized bed reactors can be used. In the typical practice of this invention the carbonyl-containing compound, arylating compound, base, and catalyst are mixed in batch, optionally with a solvent, and the resulting mixture is maintained at a temperature and pressure sufficient to prepare the alpha-arylated product.

Any solvent can be used in the process of the invention provided that it does not interfere with the formation of the alpha-aryl product. Both aprotic and protic solvents are acceptable. Suitable aprotic solvents include, but are not limited to, aromatic hydrocarbons, such as toluene and xylene, chlorinated aromatic hydrocarbons, such as dichlorobenzene; and ethers, such as tetrahydrofuran. Suitable protic solvents include, but are not limited to, water and aliphatic alcohols, such as ethanol, isopropanal, and cyclohexonal, as well as glycols and other polyols. The amount of solvent which is employed may be any amount, preferably an amount sufficient to solubilize, at least in part, the reactants and base. A suitable quantity of solvent typically ranges from about 1 to about 100 grams solvent per gram reactants. Other quantities of solvent may also be suitable, as determined by the specific process conditions and by the skilled artisan.

Generally, the reagents may be mixed together or added to a solvent in any order. If it is desirable or necessary to remove air, the solvent and reaction mixture can be sparged with a non-reactive gas, such as nitrogen, helium, or argon. The process conditions can be any operable conditions which yield the desired alpha-aryl product. Beneficially, the reaction conditions for this process are mild. For example, a preferred temperature for the process of the present invention ranges from about ambient, taken as about 22° C., to about 150° C., and preferably, from about 80° C. to about 110° C. The process may be run at subatmospheric pressures if necessary, but typically proceeds sufficiently well at about atmospheric pressure. The process is generally run for a time sufficient to convert as much of the carbonyl-containing compound to product as possible. Typical reaction times range from about 30 minutes to about 24 hours, but longer times may be used if necessary.

The product can be recovered by conventional methods known to those skilled in the art, including, for example, distillation, crystallization, sublimation, and gel chromatography. The yield of product will vary depending upon the specific catalyst, reagents, and process conditions used. For the purposes of this invention, "yield" is defined as the mole percentage of alpha-aryl product recovered, based on the number of moles of carbonyl-containing compound employed. Typically, the yield of alpha-aryl product is greater than about 25 mole percent. Preferably, the yield of alpha-aryl product is greater than about 60 mole percent, and more preferably, greater than about 80 mole percent.

The following examples are intended to illustrate, but in no way limit the scope of the present invention. All parts and percentages are by weight and all temperatures are in degrees Celsius unless explicitly stated otherwise.

EXAMPLES 1–14

Examples 1–14 illustrate reactions of several ketones and malonates with various arylating compounds.

Reactions using tri-t-butylphosphine as ligand: The reaction conditions and results are shown in Table I. A typical procedure is given for the reaction in entry 3.

1,2-Diphenyl-1-ethanone: $Pd(OAc)_2$ (2.3 mg, 0.010 mmol), tri-t-butylphosphine (2.1 mg, 0.010 mmol) and $NaO^tBu$ (211 mg, 2.20 mmol) were suspended in 1 mL of THF in a screw-capped vial. The vial was sealed with a cap containing a PTFE septum and removed from the dry box. Bromobenzene (157 mg, 1.00 mmol) and acetophenone (132 mg, 1.10 mmol) were added to the reaction mixture by syringe. The reaction mixture was stirred at 25° C. and monitored by GC analysis. The crude reaction was diluted with ether and washed with 1N HCl, water and brine. The organic layer was dried over $Na_2SO_4$, filtered and concentrated in vacuo. The residue was chromatographed on silica gel (hexane/EtOAc=95/5) to give 188 mg (96%) of 1,2-Diphenyl-1-ethanone: $^1H$ NMR: ($CDCl_3$) δ 8.02 (d, J=7.1 Hz, 2H), 7.58–7.26 (m, 8H), 4.31 (s, 2H); $^{13}C\{^1H\}$ NMR: ($CDCl_3$) δ 197.52, 136.79, 134.67, 133.09, 129.54, 129.50, 128.64, 128.62, 126.88, 45.50.

2-(4-Benzoylphenyl)-1-phenyl-1-propanone: $Pd(OAc)_2$ (4.5 mg, 0.020 mmol), Tri-t-butylphosphine (4.1 mg, 0.020 mmol), $NaO^tBu$ (144 mg, 1.50 mmol), 4-Bromobenzophenone (261 mg, 1.00 mmol) and Propiophenone (148 mg, 1.10 mmol) were used. Reaction at 70° C. for 12 h gave 304 mg (97%) of 2-(4-Benzoylphenyl)-1-phenyl-1-propanone after silica gel chromatography (hexane/EtOAc=85/15). $^1H$ NMR: ($CDCl_3$) δ 7.96 (d, J=7.7 Hz, 2H), 7.76–7.75 (m, 4H), 7.58 (t, J=7.2 Hz, 1H), 7.52 (t, J=7.1 Hz, 1H), 7.47 (t, J=7.7 Hz, 2H), 7.43–7.40 (m, 4H), 4.79 (q, J=6.9 Hz, 1H), 1.59 (d, J=6.9 Hz, 3H); $^{13}C\{^1H\}$ NMR: ($CDCl_3$) δ 199.66, 196.14, 146.16, 137.51, 136.23, 133.10, 132.40, 130.82, 129.94, 129.80, 128.75, 128.63, 128.26, 127.79, 47.72, 19.37. MS m/e (relative intensity): 314 (10), 105 (100), 77 (38), 51 (13). Anal. Calcd for $C_{22}H_{18}O_2$: C, 84.05; H, 5.77. Found: C, 83.91: H, 5.88.

Reaction using 0.005 mol % catalyst: $Pd(OAc)_2$ (0.5 mg, 0.0023 mmol), tri-t-butylphosphine (0.4 mg, 0.0020 mmol) and $NaO^tBu$ (5.80 g, 60.3 mmol) were suspended in 5 mL of THF in a screw-capped test tube. Bromobenzene (6.28 g, 40.0 mmol) and propiophenone (5.90 g, 44.0 mmol) were added to the reaction mixture in the drybox. The reaction tube was sealed with a cap and the mixture was stirred for 24 h at 60° C. The reaction was diluted with ether and washed with water and brine. The organic layer was dried over $Na_2SO_4$, filtered and concentrated in vacuo. The residue was chromatographed on silica gel (hexane/EtOAc=95/5) to give 8.2 g (98%) of 1,2-Diphenyl-1-propanone.

Reaction of propiophenone with p-tolyltosylate: $Pd(OAc)_2$ (9.0 mg, 0.040 mmol), ligand (27.1 mg, 0.050 mmol), $NaO^tBu$ (144 mg, 1.50 mmol) and 4-methylphenyl-p-toluene sulfonate (262 mg, 1.00 mmol) were suspended in 1 mL of dioxane in a screw-capped vial. The vial was sealed with a cap containing a PTFE septum and removed from the dry box. Propiophenone (132 mg, 1.10 mmol) was added to the reaction mixture by syringe. The reaction mixture was stirred at 100° C. and monitored by GC analysis. The crude reaction was diluted with ether and washed with 1N HCl, water and brine. The organic layer was dried over Na₂SO₄, filtered and concentrated in vacuo. The residue was chromatographed on silica gel (hexane/EtOAc=95/5) to give 135 mg (60%) of 2-(4-Methoxyphenyl)-1-phenyl-1-propanone.

Reactions using tri-cyclohexylphosphine as ligand: The reaction conditions and results are shown in Table I. A typical procedure is given for the reaction in Example 8.

1,2-Diphenyl-1-propanone: Pd(OAc)₂ (4.5 mg, 0.020 mmol), Tri-cyclohexyphosphine (5.6 mg, 0.020 mmol) and NaO$^t$Bu (144 mg, 1.50 mmol) were suspended in 1 mL of THF in a screw-capped vial. The vial was sealed with a cap containing a PTFE septum and removed from the dry box. Chlorobenzene (113 mg, 1.00 mmol) and propiophenone (144 mg, 1.10 mmol) were added to the reaction mixture by syringe. The reaction mixture was stirred at 50° C. and monitored by GC analysis. The crude reaction was diluted with ether and washed with water and brine. The organic layer was dried over Na₂SO₄, filtered and concentrated in vacuo. The residue was chromatographed on silica gel (hexane/EtOAc=95/5) to give 204 mg (97%) of 1,2-Diphenyl-1-propanone.

Reaction of Malonates with aryl halides: Phenyl di-tert-butylmalonate: Pd(OAc)₂ (9.0 mg, 0.040 mmol), D$^t$BPF (23.8 mg, 0.050 mmol) and NaO$^t$Bu (288 mg, 3.00 mmol) were suspended in 2 mL of dioxane in a screw-capped vial. The vial was sealed with a cap containing a PTFE septum and removed from the dry box. Chlorobenzene (225 mg, 2.00 mmol) and di-tert-butyl malonate (480 mg, 2.20 mmol) were added to the reaction mixture by a syringe. The reaction was heated at 100° C. and monitored by GC analysis. The reaction mixture was diluted with ether and was washed with water and brine. The organic layer was dried over Na₂SO₄, filtered and concentrated in vacuo. The residue was chromatographed on silica gel (hexane/EtOAc= 80/20) to give 465 mg (80%) of phenyl di-tert-butylmalonate: $^1$H NMR: (CDCl₃) δ 7.40–7.33 (m, 5H), 4.44 (s, 1H), 1.47 (s, 18H); $^{13}$C{$^1$H} NMR: (CDCl₃) δ 167.44, 133.51, 129.30, 128.38, 127.83, 81.92, 60.10, 27.87.

Phenyl diethylmalonate: Pd(OAc)₂ (4.5 mg, 0.020 mmol), P($^t$Bu)₃ (4.1 mg, 0.020 mmol) and NaO$^t$Bu (100 mg, 1.04 mmol) were suspended in 2 mL of dioxane in a screw-capped vial. The vial was sealed with a cap containing a PTFE septum and removed from the dry box. Bromobenzene (157 mg, 1.00 mmol) and diethyl malonate (176 mg, 1.10 mmol) were added to the reaction mixture by syringe. The reaction was heated at 70° C. and monitored by GC analysis. The reaction mixture was diluted with ether and was washed with water and brine. The organic layer was dried over Na₂SO₄, filtered and concentrated in vacuo. The residue was chromatographed on silica gel (hexane/EtOAc= 80/20) to give 205 mg (86%) of phenyl diethylbutylmalonate: $^1$H NMR: (CDCl₃) δ 7.42–7.33 (m, 5H), 4.62 (s, 1H), 4.23 (q, J=7.3 Hz, 4H), 1.27 (t, J=7.3 Hz, 6H); $^{13}$C{$^1$H} NMR: (CDCl₃) δ 168.13, 132.84, 129.25, 128.56, 128.16, 61.75, 57.98, 13.98.

The results of the above experiments are summarized in I.

TABLE I

Reaction of Ketones and Malonates

| Entry | ArX | Ketone/Malonate | Product | mol % Pd, Ligand | Conditions | Yield |
|---|---|---|---|---|---|---|
| 1 | PhBr | Me–C(O)–Ph | Me–CH(Ar)–C(O)–Ph | 0.5% Pd(dba)₂, P(t-Bu)₃ | 25° C., 2 hr | 97% |
| 2 | PhBr | Me–C(O)–Ph | Me–CH(Ar)–C(O)–Ph | 0.00% Pd(dba)₂, P(t-Bu)₃ | 60° C., <24 hr | 96% |
| 3 | PhBr | H–CH₂–C(O)–Ph | Ph–CH₂–C(O)–Ph | 1% Pd(OAc)₂, P(t-Bu)₃ | 25° C., 6 hr | 96% |
| 4 | PhBr | H–C(Me)₂–C(O)–Ph | Ph–C(Me)₂–C(O)–Ph | 1% Pd(OAc)₂, P(t-Bu)₃ | 50° C., 12 hr | 92% |
| 5 | 3-Me—OC₆H₄Br | H–CH(iPr)–C(O)–H,Me | Ph–C(iPr)(Me)–C(O)–H | 1% Pd(OAc)₂, P(t-Bu)₃ | 50° C., 12 hr | 83% |

TABLE I-continued

Reaction of Ketones and Malonates

| Entry | ArX | Ketone/Malonate | Product | mol % Pd, Ligand | Conditions | Yield |
|---|---|---|---|---|---|---|
| 6 | PhBr | cyclohexanone | 2-Ph-cyclohexanone | 1% Pd(OAc)$_2$ P(t-Bu)$_3$ | 50° C., 3 hr | 73% |
| 7 | PhCl | PhC(O)CH(H)CH$_3$ | PhC(O)C(CH$_3$)(Ar-R') | 2% Pd(OAc)$_2$ P(t-Bu)$_3$ | 70° C., 4 hr | 90% |
| 8 | PhCl | PhC(O)CH(H)CH$_3$ | PhC(O)C(CH$_3$)(Ar-R') | 2% Pd(OAc)$_2$ P(Cy)$_3$ | 50° C., 12 hr | 93 |
| 9 | 3-Me—OC$_6$H$_4$Cl | iPrC(O)CH(H)CH$_3$ | iPrC(O)C(CH$_3$)(Ar-R') | 2% Pd(OAc)$_2$ P(t-Bu)$_3$ | 70° C., 12 hr | 69% |
| 10 | 4-Me—OC$_6$H$_3$Cl | Ph$_1$C(O)CH$_2$CH$_3$ | PhC(O)C(CH$_3$)(4-MeO-C$_6$H$_4$) | 2% Pd(OAc)$_2$ P(t-Bu)$_3$ | 70° C., 12 hr | 91% |
| 11 | 4-Me—OC$_6$H$_4$Cl | Ph$_1$C(O)CH$_2$CH$_3$ | PhC(O)C(CH$_3$)(4-MeO-C$_6$H$_4$) | 2% Pd(OAc)$_2$ P(Cy)$_3$ | 70° C., 12 hr | 93% |

TABLE I-continued

Reaction of Ketones and Malonates

| Entry | ArX | Ketone/Malonate | Product | mol % Pd, Ligand | Conditions | Yield |
|---|---|---|---|---|---|---|
| 12 | 3-Me—OC$_6$H$_4$Cl | (pinacolone, Me$_3$C-C(O)Me) | (2-methyl-2-(3-methoxyphenyl)-3-butanone) | 2% Pd(OAc)$_2$ P(t-Bu)$_3$ | 70° C., 12 hr | 82% |
| 13 | 4-Ph—C(O)—C$_6$H$_4$Cl | propiophenone | 2-(4-benzoylphenyl)propiophenone | 2% Pd(OAc)$_2$ P(t-Bu)$_3$ | 70° C., 24 hr | 95% |
| 14 | PhBr | diethyl malonate | diethyl phenylmalonate | 2% Pd(OAc)$_2$ P(t-Bu)$_3$ | 70° C., 3 hr | 80% |

EXAMPLES 15–21

Table II shows results for a variety of conditions for the following reaction:

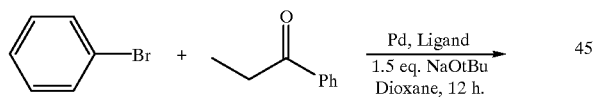

PhBr + propiophenone $\xrightarrow[\text{Dioxane, 12 h.}]{\text{Pd, Ligand} \atop \text{1.5 eq. NaOtBu}}$

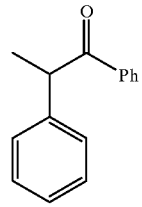

The catalyst, metal source, conditions, and yields are in Table II.

TABLE II

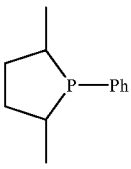

| Example | Metal | Ligand | Conditions | Yield (PhPr:Product) |
|---|---|---|---|---|
| 15 | 2% Pd(dba)$_2$ | 1.5% (2,5-dimethylphospholane-Ph) | RT | 50:50 |
| 16 | 5% Pd(dba)$_2$ | 4% tBuP(NEt$_2$)$_2$ | RT | 11:89 |
| 17 | 2% Pd(dba)$_2$ | 2% P(NEt$_2$)$_2$ | RT | No Reaction |
|  |  |  | 100° C. 6h | 0:100 |
| 18 | 2% Pd(dba)$_2$ | 1.5% P(Net$_2$)$_3$ | 50° C. | 0:100 |
| 19 | 2% Pd(dba)$_2$ | 4% P(Net$_2$)$_3$ | 50° C. | 19:81 |

TABLE II-continued

| Example | Metal | Ligand | Conditions | Yield (PhPr:Product) |
|---|---|---|---|---|
| 20 | 2% Pd(dba)$_2$ | 1.5% P(NMe$_2$)$_3$ | RT | 64:36 |
| 21 | 2% Pd(dba)$_2$ | 4% 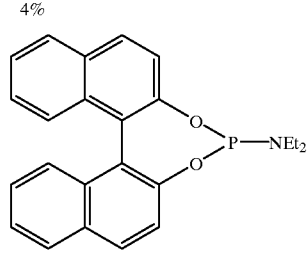 | RT | 36:64 |

These reactions demonstrate that the ligand need not contain R groups bonded to E by carbon, but can include ligands with R groups bonded to E by nitrogen and oxygen and combinations of those bonded by C, N, and O are effective ligands for these reactions.

EXAMPLES 22–31

Examples 22–31 show results of the following chemical reaction under various conditions and with various catalysts.

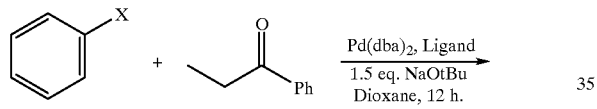

-continued

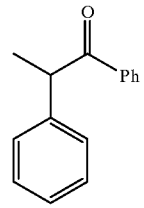

TABLE III

| Example | ArX | Pd(dba)$_2$ | Ligand | Temp. | ArX = Product |
|---|---|---|---|---|---|
| 22 | PhCl | 5 mol % | 4 mol % tBuP(NEt$_2$)$_2$ | 100° C. | 0:100 |
| 23 | 4-ClC$_6$H$_4$OMe | 2 mol % | 4% (binaphthyl phosphoramidite) | 70° C., 100° C., 24 h | No Reaction 9:91 |
| 24 | 4-ClC$_6$H$_4$OMe | 2 mol % | 1.5% (binaphthyl phosphoramidite) | 70° C., 100° C., 24 h | No Reaction No Product |

TABLE III-continued

| Example | ArX | Pd(dba)$_2$ | Ligand | Temp. | ArX = Product |
|---|---|---|---|---|---|
| 25 | PhBr | 5 mol % | 4 mol% 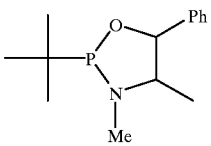 | RT | 3:97 |
| 26 | 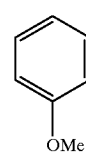 | 5 mol % | 4 mol % tBu(NEt$_2$)$_3$ | 100° C. | 0:100 |
| 27 | PhBr | 5 mol % | 4 mol % (iPr$_2$)PNEt$_2$ | RT | 15:85 |
| 28 | PhBr | 5 mol % | 4 mol % (tBu$_2$)PNEt$_2$ | RT | 6:94 |
| 29 | PhBr | 5 mol % | 4 mol % Ph—P(NEt$_2$)$_2$ | RT | 29:71 |
| 30 | PhBr | 5 mol % | 4 mol % 2,8,9-Trimethyl-1-phospha-2,5,8,9-tetraazabicyclo[3.3.3]undecane | RT | 55:45 |
| 31 | PhBr | 5 mol % | 4 mol % 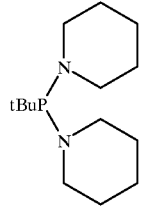 | RT | 20:80 |

These results demonstrate that catalyts containing the ligands with R groups bonded to E through oxygen and nitrogen are capable of reacting with aryl chlorides as well as aryl bromides.

EXAMPLES 32–34

The catalyst $X_nM(ER_{1-4})_m$ may also be a chiral catalyst. In this case one can use a non-racemic chiral catalyst to generate non-racemic products. This asymmetric version of the reaction is evidenced by the optical activity of the purified α-arylketone products (Table IV).

TABLE IV

| Example | ArX | Substrate | Catalyst | Optical Rotation |
|---|---|---|---|---|
| 32 | PhBr | 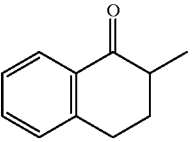 | 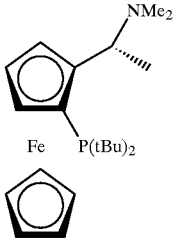 | $[\alpha]_D^{20} = 8.4$ (c = 1.00, CHCl$_3$) |

TABLE IV-continued

| Example | ArX | Substrate | Catalyst | Optical Rotation |
|---|---|---|---|---|
| 33 | PhBr | 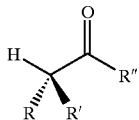 | (1-naphthyl with OMe and PPh₂ substituents on 2-naphthyl) | $[\alpha]_D^{20} = -3.2$ (c = 1.00, CHCl₃) |
| 34 | PhBr | 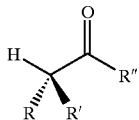 | (1-naphthyl with OMe and PPh₂ substituents on 2-naphthyl, opposite enantiomer) | $[\alpha]_D^{20} = 0.5$ (c = 1.00, CHCl₃) |

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A process for preparing an alpha-arylated or -vinylated carbonyl compounds, comprising the step of:

reacting a compound having at least one carbonyl group and an atom alpha to said carbonyl group bearing at least one hydrogen atom with an arylating or vinylating compound selected from the group consisting of ketone, amides, esters, carboxylic acids, thioesters, amidines, anhydrides, β-dicarbonyl compounds, α-dicarbonyl compounds, malononitriles, compounds with carbonyl groups β- to sulfoxides, sulfones, phosphates, phosphate esters, and nitriles in the presence of a base and a transition metal catalyst under reaction conditions effective to form said alpha-arylated or vinylated carbonyl compound, said transition metal catalyst having the formula:

$$X_nM(ER_{1-4})_m$$

wherein X is an optional ligand, M is a group 8 transition metal, E is an element bearing a nonbonding electron pair when E is not bonded to the metal, and R is a substituent bonded to E through a carbon, nitrogen, oxygen, or sulfur atom, with the proviso that R₃ cannot contain 3 aryl groups, n is an integer from 0 to 4, and m is an integer from 1–4.

2. The process of claim 1, wherein said compound having at least one carbonyl group and an atom alpha to said carbonyl group bearing at least one hydrogen atom is selected from those having the structure

where R and R' are independently selected from the group consisting of hydrogen, alkyl, aryl or heteroaryl, alkoxo, vinyl, alkyl, and amido; and R" is selected from the group consisting of hydrogen, aryl or heteroaryl, alkoxo, vinyl, alkyl, and amido.

3. The process of claim 1, wherein said compound having at least one carbonyl group and an atom alpha to said carbonyl group bearing at least one hydrogen atom is selected from the group consisting of acetophenone, propiophenone, isobutyrophenone, acetone, and diethyl ketone.

4. The process of claim 1, wherein said arylating compound is selected from the group consisting of 5, 6, or 7-membered aryl ring structures comprising an activated group.

5. The process of claim 4, wherein said arylating compound is selected from those having the structure

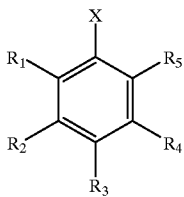

wherein X is a halogen atom or a sulfur-containing leaving group, and R₁, R₂, R₃, R₄, and R₅ are selected from the group consisting of H; CN; alkyl, vinyl, alkenyl, formyl; CF₃; CCl₃; halide, C₆H₅, amide, C(O)N(CH₃)₂, C(O)N(CH₂CH₃)₂, C(O)N(CH₂CH₂CH₃)₂, acyl, C(O)—C₆H₅, ester, aryl, alkoxy, thioalkoxy, phosphino, amino, and heterocyclic.

6. The process of claim 4, wherein said arylating compound is selected from those having the structure

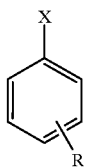

wherein X is Br or Cl, and R is p-CN, m-CN, p-t-Bu, m-OMe, p-OMe o-Me, p-C(O)H, p-CF$_3$, p-Ph, p-C(O)Et$_2$, p-H, and p-C(O)Ph.

7. The process of claim 1, wherein said vinylating compound is selected from the group consisting of vinyl halides, vinyl sulfonates, vinyl tosylates, and vinyl phosphates.

8. The process of claim 1, wherein said base is selected from the group consisting of alkali metal hydroxides, alkali metal alkoxides, metal carbonates, alkali metal amides, alkali metal aryl oxides, tertiary amines, tetraalkylammonium hydroxides, diaza organic bases, and silyl bases.

9. The process of claim 1, wherein said Group 8 metal is selected from the group consisting of palladium, platinum, and nickel.

10. The process of claim 1, wherein said optional ligand is selected from the group consisting of halide, acetate, and alkene.

11. The process of claim 1, wherein L is an atom selected from Group 14, 15, or 16 of the Periodic Table.

12. The process of claim 11, wherein L is phosphorous.

13. The method of claim 1, wherein R is a substituent selected from the group consisting of alkyl, cycloalkyl, aryl, alkoxo, amido, cyclic, and heterocyclic.

14. The method of claim 1, wherein said R is selected from the group consisting of t-butyl, N(CH$_2$CH$_3$)$_2$, cyclohexyl, cyclohexyl, dialkylamino, o-tolyl, o-anisyl, phenyl, 2-biphenylyl, ferrocenyl, and substituted ferrocenyl.

15. The process of claim 1, wherein said catalyst is prepared in situ in the reaction mixture.

16. The process of claim 15, wherein the catalyst is prepared from an alkene or diene complex of a Group 8 transition metal complex or a Group 8 transition metal carboxylate.

17. The process of claim 1, wherein the alkene complex of the Group 8 transition metal is di(benzylidene)acetone.

18. The process of claim 1, wherein the catalyst is anchored or supported on a catalyst support.

19. The process of claim 1, wherein said reaction conditions further comprise a solvent selected from the group consisting of aromatic hydrocarbons, chlorinated aromatic hydrocarbons, ethers, water, and aliphatic alcohols.

20. The process of claim 1, further comprising the step of isolating said alpha-arylated carbonyl compound.

21. The process of claim 1, wherein said transition metal catalyst is a non-racemic chiral catalyst and generates a non-racemic product having optical activity.

* * * * *